(12) United States Patent
Shpayer et al.

(10) Patent No.: US 11,963,494 B2
(45) Date of Patent: *Apr. 23, 2024

(54) SCABIOSA ATROPURPUREA PLANTS AND METHODS OF PRODUCING SAME

(71) Applicant: Danziger Dan Flower Farm, Moshav Mishmar HaShiva (IL)

(72) Inventors: Noam Shpayer, Yahud (IL); Gavriel Danziger, Moshav Nir-Zvi (IL)

(73) Assignee: Danziger Dan Flower Farm, Moshav Mishmar HaShiva (IL)

( * ) Notice: Subject to any disclaimer, the term of this patent is extended or adjusted under 35 U.S.C. 154(b) by 140 days.

This patent is subject to a terminal disclaimer.

(21) Appl. No.: 16/645,817

(22) PCT Filed: Sep. 12, 2018

(86) PCT No.: PCT/IL2018/051025
§ 371 (c)(1),
(2) Date: Mar. 10, 2020

(87) PCT Pub. No.: WO2019/053718
PCT Pub. Date: Mar. 21, 2019

(65) Prior Publication Data
US 2020/0329656 A1    Oct. 22, 2020

Related U.S. Application Data

(60) Provisional application No. 62/695,082, filed on Jul. 8, 2018, provisional application No. 62/557,185, filed on Sep. 12, 2017.

(51) Int. Cl.
*A01H 6/12* (2018.01)
*A01H 1/00* (2006.01)
*A01H 5/02* (2018.01)
*A01H 6/00* (2018.01)

(52) U.S. Cl.
CPC ............ *A01H 1/1215* (2021.01); *A01H 5/02* (2013.01); *A01H 6/00* (2018.05)

(58) Field of Classification Search
CPC ..................................................... A01H 5/02
USPC ......................................................... Plt./478
See application file for complete search history.

(56) References Cited

U.S. PATENT DOCUMENTS

| PP24,652 P2 | 7/2014 | Robb | |
|---|---|---|---|
| PP29,621 P3 * | 8/2018 | Danziger | A01H 5/02 Plt./478 |
| PP29,622 P3 * | 8/2018 | Danziger | A01H 5/02 Plt./478 |

FOREIGN PATENT DOCUMENTS

| EP | 2189474 | 5/2010 |
|---|---|---|
| JP | 09-266725 | 10/1997 |
| JP | 2008-211968 | 9/2008 |
| JP | 2010-535477 | 11/2010 |
| JP | 2011-502523 | 1/2011 |
| JP | 2017-508477 | 3/2017 |
| WO | WO2009/062259 | 5/2009 |
| WO | WO 2015/110635 | 7/2015 |
| WO | WO 2019/053718 | 3/2019 |

OTHER PUBLICATIONS

Wielgolaski, F.E. Oikos vol. 18, No. 1, pp. 1-13 (Year: 1967).*
Johnny's Selected Seeds online catalog Product ID: 1690 Scabiosa atropurpurea Olympia Mix (F1) (Year: 2006).*
Johnny's Selected Seeds online catalog p. 162 Product ID: 1690 Scabiosa atropurpurea Olympia Mix (F1) (Year: 2009).*
Taylor et al Acta Hort. vol. 664, pp. 647-652 (Year: 2004).*
International Preliminary Report on Patentability dated Mar. 26, 2020 From the International Bureau of WIPO Re. Application No. PCT/IL2018/051025. (8 Pages).
International Search Report and the Written Opinion dated Dec. 12, 2018 From the International Searching Authority Re. Application No. PCT/IL2018/051025. (15 Pages).
Gaze "Sabiosa, Imperial Mix", The Seed Company by E. W. Gaze, XP002786515, Retrieved From the Internet, 2 P., Nov. 15, 2018.
Hanks "Field- and Tunnel-Grown Cut-Flowers With Potential for UK Exploitation: A Review of Trials Programmes and Research on 'Novel' Subjects", Horticulture Development Company, The National Cut Flower Centre, XP002786517, p. 1-17, Oct. 1, 2013.
Iglehart "2014 Order Form", Susan Iglehart's Flowers, XP002786516, Retrieved From the Internet, Jan. 1, 2014.
Thompson et al. "Scabiosa Atropurpurea 'Beaujolais Bonnets'", Thompson & Morgan, Wholesale Seeds & Vegetative Breeding, Web Site, 2 P., 2017.
West Coast Seeds "Imperial Mix", West Coast Seeds, XP002786514, Retrieved From the Internet, 2 P., Nov. 15, 2018.
Communication Pursuant to Article 94(3) EPC dated Feb. 11, 2021 From the European Patent Office Re. Application No. 18789706.1. (5 Pages).
Notification of Office Action dated Jun. 9, 2020 From the State Intellectual Property Office of the People's Republic of China Re. Application No. 201880073671.7 and Its Summary in English. (3 Pages).
Examination Report dated May 22, 2022 From the Republica de Colombia, Superintendencia de Industria y Comercio Re. Applikcation No. NC2020/0004331 with its English Summary. (4 Pages).
English Translation dated May 27, 2022 of Notice of Reasons for Rejection dated Apr. 25, 2022 From the Japan Patent Office Re. Application No. 2020-515867. (8 Pages).
Liu et al. "Flowering Characteristics and Pollination Ecology of Scabiosa Tschiliensis", Acta Ecologica Sinica, 24(4):718-723, Apr. 25, 2004. English Abstract.

(Continued)

*Primary Examiner* — David H Kruse

(57) ABSTRACT

A *Scabiosa atropurpurea* plant characterized by an inflorescence diameter above 7 cm is provided. Also provided are a *Scabiosa atropurpurea* plant characterized by a pedicel length above 60 cm, and a *Scabiosa atropurpurea* plant characterized by a pedicel diameter above 5 mm.

4 Claims, 8 Drawing Sheets

(56) References Cited

OTHER PUBLICATIONS

Wu et al. "Mongolia Chervil ( Scabiosa Comosa Fisch) With Two Kinds of Variation Form and the Content of Chlorogenic Acid", Journal of Medicine and Pharmacy of Chinese Minorities, 2: 38-39, Feb. 28, 2016. English Abstract.
Notice of Reasons for Rejection dated Apr. 25, 2022 From the Japan Patent Office Re. Application No. 2020-515867. (5 Pages).
Ace of Spades Scab Iosa Atropurpurea ' Ace of Spades', Pinsushion F lower ' Ace of Spa, Retrieved from Internet: 1P., Published Online May 12, 2015.
Krizek et al. "Control of Flower Size", Journal of Experimental Botany, 64(6): 1427-1437, Published Feb. 11, 2013.
Pincushion Flower North Carolina Extension Gardener Plant Toolbox, Scab Iosa Atropurpurea: 2P.,Retrieved from Internet, Published Online May 19, 2020.
Notification of Office Action and Search Report dated May 9, 2022 From the State Intellectual Property Office of the People's Republic of China Re. Application No. 201880073671.7 and its Translation into English. (5 Pages).
Communication Pursuant to Article 94(3) EPC dated Apr. 7, 2022 From the European Patent Office Re. Application No. 18789706.1. (6 Pages).
Decision of Rejection dated Nov. 8, 2022 From the Japan Patent Office Re. Application No. 2020-515867 and Its Translation Into English.(3 pages).
Examination Report dated Nov. 28, 2022 From the Republica de Colombia, Superintendencia de Industria y Comercio Re. Applikcation No. NC2020/0004331 with its English Summary and Claims. (11 Pages).
Notification of Office Action dated Dec. 13, 2022 From the State Intellectual Property Office of the People's Republic of China Re. Application No. 201880073671.7 and Its Translation Into English. (10 Pages).
Notification of Substantive Examination Report/Invitation to Amend Application dated Nov. 27, 2022 From the Kenya Industrial Property Institute, Re Application No. KE/P/2020/3619. (3 Pages).
BBB Sccd "Pincushion Flower—Scabiosa atropurpurea 'Imperial Mix'", retrieved from the internet: https://bbbseed.com/product/pincushion-flower-scabiosa-atropurpurea-imperial-mix/.(4 pages).
Communication Pursuant to Article 94(3) EPC dated Jun. 28, 2023 From the European Patent Office Re. Application No. 18789706.1. (6 Pages).
Office Action dated Jul. 6, 2023 From the Israel Patent Office Re. Application No. 273280. (5 Pages).
Notification of Office Action dated Apr. 27, 2023 From the State Intellectual Property Office of the People's Republic of China Re. Application No. 201880073671.7 and Its Translation Into English. (7 Pages).
Examination Report dated Jul. 31, 2023 From The Republica De Columbia Superintendencia De Industria Y Comerciio Re. Application No. NC2020/0004331 and its Machine Translation. (14 Pages).

* cited by examiner

SCABIOSA ATROPURPUREA PLANTS AND METHODS OF PRODUCING SAME

RELATED APPLICATIONS

This application is a National Phase of PCT Patent Application No. PCT/IL2018/051025 having International filing date of Sep. 12, 2018, which claims the benefit of priority under 35 USC § 119(e) of U.S. Provisional Patent Application Nos. 62/695,082 filed on Jul. 8, 2018 and 62/557,185 filed on Sep. 12, 2017. The contents of the above applications are all incorporated by reference as if fully set forth herein in their entirety.

FIELD AND BACKGROUND OF THE INVENTION

The present invention, in some embodiments thereof, relates to *Scabiosa atropurpurea* plants and methods of producing same.

*Scabiosa atropurpurea* is counted among the dipsacaeaea family (USDA). The Family Dipsacaeae is a small family of about 150 species in eight genera. Family Dipsacaceae is distributed mainly in Europe, Asia, Africa, especially Mediterranean region. Genera include *Scabiosa* (100 spp.), Knautia (50 spp.) and Dipsacus (15 spp.) (Boulos, 2002, Flora of Egypt Vol. 3). The genus *Scabiosa* is taxonomically the most important member of the Dipsacaceae in terms of complexity (Verlaque, 1986a Etude biosystematique et phylogénétique desDipsacaceae. IV.—Tribus desScabioseae (phylum n° 1, 2, 3).—Rev. Cytol. Biol. Veg. Le Botaniste9: 5-72; Verlaque, 1986b Etude biosystematique et phylogénétique desDipsacaceae. V. Tribus desScabioseae (phylum n° 4) et conclusion.—Rev. Cytol. Biol. Veg. Le Botaniste9: 97-176). The Genus is present mainly in temperate Eurasia, Mediterranean region, East African mountains, South Africa (Boulos, 2002 Flora of Egypt Vol. 3).

The *Scabiosa* genus includes annual or perennial herbs, often heterophyllous. *Scabiosa Atropurpurea* is marketed and sold for many years as garden plants (Kinzler varieties for example) in Europe and the U.S. Only in the recent years *Scabiosa Atropurpurea* varieties marketing as a cut flower in the US and Europe has started (pioneered by Danziger Dan Flower Farm and followed by Hillverda Kooji).

BUDAPEST TREATY DEPOSIT

The biological materials that are the subject of the instant application were deposited and have been accepted by the International Depository Authority under the Budapest Treaty. Specifically, SB-15-1483, seeds of which have been deposited under the Budapest Treaty at the Korean Collection for Type Cultures under KCTC13541BP on Jun. 5, 2018; SB-15-1484, seeds of which have been deposited under the Budapest treaty at the NCIMB Ltd. (Ferguson Building Craibstone Estate, Bucksburn. Aberdeen Scotland) under NCIMB43095 on Jul. 11, 2018; SB-15-1503, seeds of which have been deposited under the Budapest treaty at the NCIMB Ltd. (Ferguson Building Craibstone Estate, Bucksburn. Aberdeen Scotland) under NCIMB43096 on Jul. 11, 2018; SB-15-1504, seeds of which have been deposited under the Budapest Treaty at the Korean Collection for Type Cultures under KCTC13542BP on Jun. 5, 2018; SB-15-1577, seeds of which have been deposited under the Budapest treaty at the NCIMB Ltd. (Ferguson Building Craibstone Estate, Bucksburn. Aberdeen Scotland) under NCIMB43141 on Aug. 6, 2018; SB-16-1593, seeds of which have been deposited under the Budapest treaty at the NCIMB Ltd. (Ferguson Building Craibstone Estate, Bucksburn. Aberdeen Scotland) under NCIMB43139 on Jul. 11, 2018; SB-16-1597, seeds of which have been deposited under the Budapest treaty at the NCIMB Ltd. (Ferguson Building Craibstone Estate, Bucksburn. Aberdeen Scotland) under NCIIVIB43142 on Aug. 6, 2018; SB-15-1575, seeds of which have been deposited under the Budapest treaty at the NCIMB Ltd. (Ferguson Building Craibstone Estate, Bucksburn. Aberdeen Scotland) under NCIMB43138 on Jul. 11, 2018; SB-15-1574, seeds of which have been deposited under the Budapest treaty at the NCIMB Ltd. (Ferguson Building Craibstone Estate, Bucksburn. Aberdeen Scotland) under NCIIVIB43140 on Aug. 6, 2018; SB-15-1550, seeds of which have been deposited under the Budapest Treaty at the Korean Collection for Type Cultures under KCTC13543BP on Jun. 5, 2018; SB-15-1592, seeds of which have been deposited under the Budapest Treaty at the Korean Collection for Type Cultures under KCTC13545BP on Jun. 5, 2018; SB-16-1539, seeds of which have been deposited under the Budapest treaty at the NCIMB Ltd. (Ferguson Building Craibstone Estate, Bucksburn. Aberdeen Scotland) under NCIMB43099 on Jul. 11, 2018; SB-16-1576, seeds of which have been deposited under the Budapest Treaty at the Korean Collection for Type Cultures under KCTC13547BP on Jun. 5, 2018; SB-15-1496, seeds of which have been deposited under the Budapest treaty at the NCIMB Ltd. (Ferguson Building Craibstone Estate, Bucksburn. Aberdeen Scotland) under NCIMB43070 on Jun. 5, 2018; SB-16-1528, seeds of which have been deposited under the Budapest treaty at the NCIMB Ltd. (Ferguson Building Craibstone Estate, Bucksburn. Aberdeen Scotland) under NCIMB43071 on Jun. 5, 2018; and SB-16-1589, seeds of which have been deposited under the Budapest treaty at the NCIMB Ltd. (Ferguson Building Craibstone Estate, Bucksburn. Aberdeen Scotland) under NCIMB43072, on Jun. 5, 2018; SB-14-1434, seeds of which have been deposited under the Budapest treaty at the NCIMB Ltd. (Ferguson Building Craibstone Estate, Bucksburn. Aberdeen Scotland) under NCIMB43094, on Jul. 11, 2018; SB-15-1515, seeds of which have been deposited under the Budapest treaty at the NCIMB Ltd. (Ferguson Building Craibstone Estate, Bucksburn. Aberdeen Scotland) under NCIMB43097, on Jul. 11, 2018; SB-15-1521, seeds of which have been deposited under the Budapest treaty at the NCIMB Ltd. (Ferguson Building Craibstone Estate, Bucksburn. Aberdeen Scotland) under NCIMB43098, on Jul. 11, 2018; SB-16-1555, seeds of which have been deposited under the Budapest treaty at the NCIMB Ltd. (Ferguson Building Craibstone Estate, Bucksburn. Aberdeen Scotland) under NCIMB43100, on Jul. 11, 2018; SB-16-1562, seeds of which have been deposited under the Budapest treaty at the NCIMB Ltd. (Ferguson Building Craibstone Estate, Bucksburn. Aberdeen Scotland) under NCIMB43101, on Jul. 11, 2018.

These materials will be irrevocably and without restriction or condition released to the public upon the issuance of a patent, and the materials will be replaced if useable samples cannot be dispensed by the Depository.

SUMMARY OF THE INVENTION

According to an aspect of some embodiments of the present invention there is provided a *Scabiosa atropurpurea* plant characterized by an inflorescence diameter above 7 cm.

According to an aspect of some embodiments of the present invention there is provided a *Scabiosa atropurpurea* plant characterized by a pedicel length above 60 cm.

According to an aspect of some embodiments of the present invention there is provided a *Scabiosa atropurpurea* plant characterized by a pedicel diameter above 5 mm.

According to an aspect of some embodiments of the present invention there is provided a *Scabiosa atropurpurea* plant characterized by a pedicel length above 60 cm and a pedicel diameter above 5 mm.

According to some embodiments of the invention, the plant has a pedicel length above 60 cm.

According to some embodiments of the invention, the plant has a pedicel diameter above 5 mm.

According to some embodiments of the invention, the plant has a pedicel length below 60 cm.

According to some embodiments of the invention, the plant has a pedicel diameter below 5 mm.

According to some embodiments of the invention, the inflorescence refers to a first inflorescence of the plant.

According to some embodiments of the invention, the plant is characterized by an inflorescence diameter of at least 8 cm.

According to some embodiments of the invention, the inflorescence comprises a ray floret exhibiting at least 10% increase in floret number as compared to that of the *Scabiosa atropurpurea* plants in the same developmental stage and control growth conditions.

According to some embodiments of the invention, anthesis of florets of a disc floret of said inflorescence and anthesis of florets of a ray floret of said inflorescence occurs simultaneously.

According to some embodiments of the invention, anthesis of florets of a disc floret of said inflorescence occurs 2-3 days following anthesis of florets of a ray floret of said inflorescence.

According to some embodiments of the invention, anthesis of florets of a disc floret of said inflorescence occurs 3 days following anthesis of florets of a ray floret of said inflorescence.

According to some embodiments of the invention, the inflorescence comprises a disc floret exhibiting at least 10% increase in floret number as compared to that of the *Scabiosa atropurpurea* plants in the same developmental stage and control growth conditions.

According to some embodiments of the invention, the plant has Lavender Scoop™, Cherry Vanilla Scoop™, Blackberry Scoop™, Marshmallow Scoop™ and Vanilla Scoop™ as an ancestor thereof.

According to some embodiments of the invention, seeds of the plant are selected from the group consisting of SB-15-1483, seeds of which having been deposited under the Budapest Treaty at the Korean Collection for Type Cultures under KCTC13541BP on Jun. 5, 2018; SB-15-1484, seeds of which having been deposited under the Budapest treaty at the NCIMB Ltd. (Ferguson Building Craibstone Estate, Bucksburn. Aberdeen Scotland) under NCIMB43095 on Jul. 11, 2018; SB-15-1503, seeds of which having been deposited under the Budapest treaty at the NCIMB Ltd. (Ferguson Building Craibstone Estate, Bucksburn. Aberdeen Scotland) under NCIMB43096 on Jul. 11, 2018; SB-15-1504, seeds of which having been deposited under the Budapest Treaty at the Korean Collection for Type Cultures under KCTC13542BP on Jun. 5, 2018; SB-15-1577, seeds of which having been deposited under the Budapest treaty at the NCIMB Ltd. (Ferguson Building Craibstone Estate, Bucksburn. Aberdeen Scotland) under NCIMB43141 on Aug. 6, 2018; SB-16-1593, seeds of which having been deposited under the Budapest treaty at the NCIMB Ltd. (Ferguson Building Craibstone Estate, Bucksburn. Aberdeen Scotland) under NCIMB43139 on Jul. 11, 2018; SB-16-1597, seeds of which having been deposited under the Budapest treaty at the NCIMB Ltd. (Ferguson Building Craibstone Estate, Bucksburn. Aberdeen Scotland) under NCIMB43142 on Aug. 6, 2018; SB-15-1575, seeds of which having been deposited under the Budapest treaty at the NCIMB Ltd. (Ferguson Building Craibstone Estate, Bucksburn. Aberdeen Scotland) under NCIMB43138 on Jul. 11, 2018; SB-15-1574, seeds of which having been deposited under the Budapest treaty at the NCIMB Ltd. (Ferguson Building Craibstone Estate, Bucksburn. Aberdeen Scotland) under NCIMB43140 on Aug. 6, 2018; SB-15-1550, seeds of which having been deposited under the Budapest Treaty at the Korean Collection for Type Cultures under KCTC13543BP on Jun. 5, 2018; SB-15-1592, seeds of which having been deposited under the Budapest Treaty at the Korean Collection for Type Cultures under KCTC13545BP on Jun. 5, 2018; SB-16-1539, seeds of which having been deposited under the Budapest treaty at the NCIMB Ltd. (Ferguson Building Craibstone Estate, Bucksburn. Aberdeen Scotland) under NCIMB43099 on Jul. 11, 2018; SB-16-1576, seeds of which having been deposited under the Budapest Treaty at the Korean Collection for Type Cultures under KCTC13547BP on Jun. 5, 2018; SB-15-1496, seeds of which having been deposited under the Budapest treaty at the NCIMB Ltd. (Ferguson Building Craibstone Estate, Bucksburn. Aberdeen Scotland) under NCIMB43070 on Jun. 5, 2018; SB-16-1528, seeds of which having been deposited under the Budapest treaty at the NCIMB Ltd. (Ferguson Building Craibstone Estate, Bucksburn. Aberdeen Scotland) under NCIMB43071 on Jun. 5, 2018; and SB-16-1589, seeds of which having been deposited under the Budapest treaty at the NCIMB Ltd. (Ferguson Building Craibstone Estate, Bucksburn. Aberdeen Scotland) under NCIMB43072, on Jun. 5, 2018; SB-14-1434, seeds of which having been deposited under the Budapest treaty at the NCIMB Ltd. (Ferguson Building Craibstone Estate, Bucksburn. Aberdeen Scotland) under NCIMB43094, on Jul. 11, 2018; SB-15-1515, seeds of which having been deposited under the Budapest treaty at the NCIMB Ltd. (Ferguson Building Craibstone Estate, Bucksburn. Aberdeen Scotland) under NCIMB43097, on Jul. 11, 2018; SB-15-1521, seeds of which having been deposited under the Budapest treaty at the NCIMB Ltd. (Ferguson Building Craibstone Estate, Bucksburn. Aberdeen Scotland) under NCIMB43098, on Jul. 11, 2018; SB-16-1555, seeds of which having been deposited under the Budapest treaty at the NCIMB Ltd. (Ferguson Building Craibstone Estate, Bucksburn. Aberdeen Scotland) under NCIMB43100, on Jul. 11, 2018; SB-16-1562, seeds of which having been deposited under the Budapest treaty at the NCIMB Ltd. (Ferguson Building Craibstone Estate, Bucksburn. Aberdeen Scotland) under NCIMB43101, on Jul. 11, 2018.

According to an aspect of some embodiments of the present invention there is provided a part of the plant as described herein.

According to some embodiments of the invention, the part of the plant is selected from the group consisting of pedicel, leaf, pollen, embryo, cotyledon, hypocotyls, meristem, root, root tip, pistil, anther, flower, floret, stem, ovule, seed and petiole.

According to an aspect of some embodiments of the present invention there is provided a flower of the plant as described herein.

According to some embodiments of the invention, the flower is a cut-flower.

According to an aspect of some embodiments of the present invention there is provided a pollen of the plant as described herein.

According to an aspect of some embodiments of the present invention there is provided a seed of the plant as described herein.

According to an aspect of some embodiments of the present invention there is provided an ovule of the plant as described herein.

According to an aspect of some embodiments of the present invention there is provided a cutting of the plant as described herein.

According to an aspect of some embodiments of the present invention there is provided a tissue culture comprising cells of the plant as described herein.

According to some embodiments of the invention, the plant is a hybrid plant.

According to some embodiments of the invention, the plant is an inbred plant.

According to an aspect of some embodiments of the present invention there is provided a method of developing the plant as described herein, the method comprising:
  (a) growing *Scabiosa atropurpurea* plants under a cover to result in reduced solar radiation conditions; and
  (b) selecting a plant of the plants that exhibits an inflorescence having a larger diameter, pedicel length and/or pedicel diameter than that of the *Scabiosa atropurpurea* plants in the same developmental stage and control growth conditions.

According to some embodiments of the invention, the method further comprises selfing or crossing the plant or plants and selecting for the inflorescence having the larger diameter, pedicel length and/or pedicel diameter.

According to some embodiments of the invention, the inflorescence comprises a ray floret exhibiting at least 10% increase in floret number as compared to that of the *Scabiosa atropurpurea* plants in the same developmental stage and control growth conditions.

According to some embodiments of the invention, the inflorescence comprises a disc floret exhibiting at least 10% increase in floret number as compared to that of the *Scabiosa atropurpurea* plants in the same developmental stage and control growth conditions.

According to some embodiments of the invention, the method further comprises selecting for pedicel length and/or pedicel diameter.

According to some embodiments of the invention, the growing is under a temperature not exceeding 25° C.

According to some embodiments of the invention, the growing is in a greenhouse or tunnel.

According to some embodiments of the invention, the greenhouse or tunnel is covered by a polyethene film.

According to some embodiments of the invention, the polyethylene sheet has substantially the same specification as that of "SUN-SELECTOR" AV thermal IR, C400 IR AV DIFF-120 micron, Genigar, Israel.

According to some embodiments of the invention, the reduced radiation is at least 40% reduction in PAR radiation of the solar radiation out of the greenhouse or tunnel.

According to some embodiments of the invention, the reduced radiation is at least 90% reduction in UV radiation of the solar radiation out of the greenhouse or tunnel.

According to an aspect of some embodiments of the present invention there is provided a *Scabiosa atropurpurea* plant obtainable according to the method as described herein.

According to an aspect of some embodiments of the present invention there is provided a method of producing a *Scabiosa atropurpurea* plant, the method comprising:
  (a) crossing the plant as described herein with another *Scabiosa atropurpurea* plant as described herein, wherein the plant and another plant are of different genetic backgrounds;
  (b) recovering seeds following the crossing;
  (c) planting the seeds and growing the seed into plants; and
  (d) selecting a hybrid plant.

According to some embodiments of the invention, the selecting is according to inflorescence diameter.

According to an aspect of some embodiments of the present invention there is provided a hybrid plant or part thereof produced according to the method as described herein.

According to an aspect of some embodiments of the present invention there is provided a method of developing a cultivated plant using plant breeding techniques, the method comprising using the plant or plant part as described herein as a source of breeding material for self-breeding and/or cross-breeding.

According to an aspect of some embodiments of the present invention there is provided a *Scabiosa atropurpurea* plant selected from the group consisting of SB-15-1483, seeds of which having been deposited under the Budapest Treaty at the Korean Collection for Type Cultures under KCTC13541BP; SB-15-1484; SB-15-1503; SB-15-1504, seeds of which having been deposited under the Budapest Treaty at the Korean Collection for Type Cultures under KCTC13542BP; SB-15-1577; SB-15-1597; SB-15-1575, seeds of which having been deposited under the Budapest Treaty at the Korean Collection for Type Cultures under KCTC13544BP; SB-15-1574; SB-15-1550, seeds of which having been deposited under the Budapest Treaty at the Korean Collection for Type Cultures under KCTC13543BP; SB-15-1592, seeds of which having been deposited under the Budapest Treaty at the Korean Collection for Type Cultures under KCTC13545BP; SB-15-1576, seeds of which having been deposited under the Budapest Treaty at the Korean Collection for Type Cultures under KCTC13547BP; SB-15-1496, seeds of which having been deposited under the Budapest treaty at the NCIMB Ltd. (Ferguson Building Craibstone Estate, Bucksburn. Aberdeen Scotland) under NCIMB43070; SB-15-1528, seeds of which having been deposited under the Budapest treaty at the NCIMB Ltd. (Ferguson Building Craibstone Estate, Bucksburn. Aberdeen Scotland) under NCIMB43071 and SB-16-1589, seeds of which having been deposited under the Budapest treaty at the NCIMB Ltd. (Ferguson Building Craibstone Estate, Bucksburn. Aberdeen Scotland) under NCIMB43072 for which representative seeds have been deposited.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
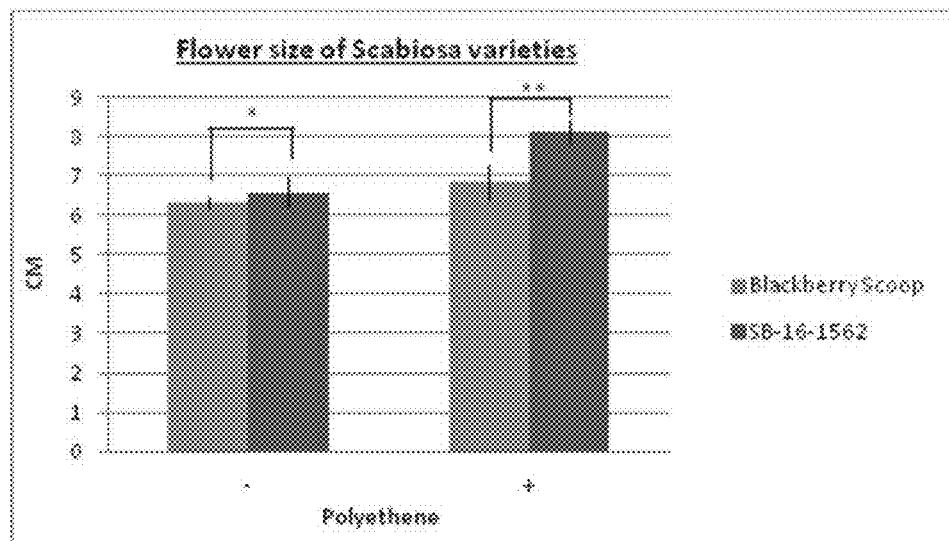
FIGS. 1A-O are bar graphs showing characteristics of plants from various genetic backgrounds obtained according to some embodiments of the invention.
Figure 1B:
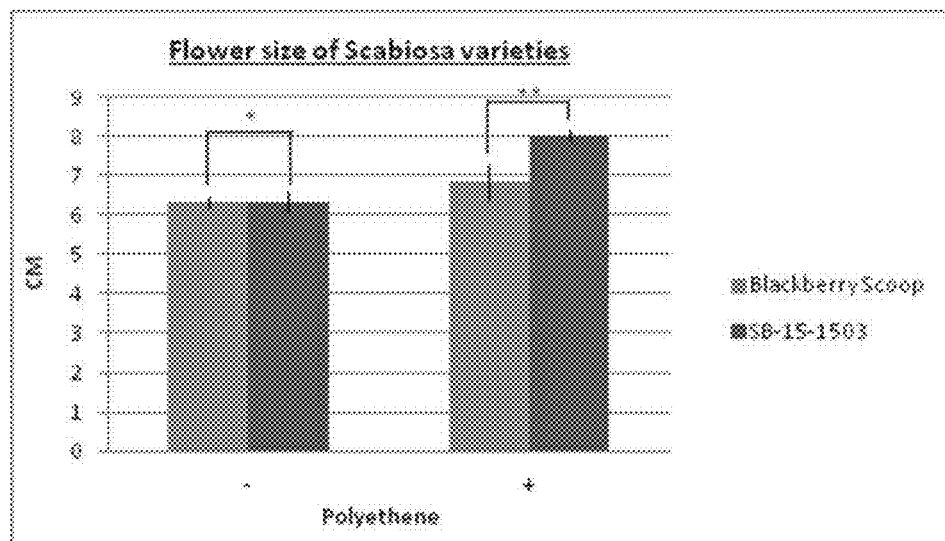
Figure 1C:
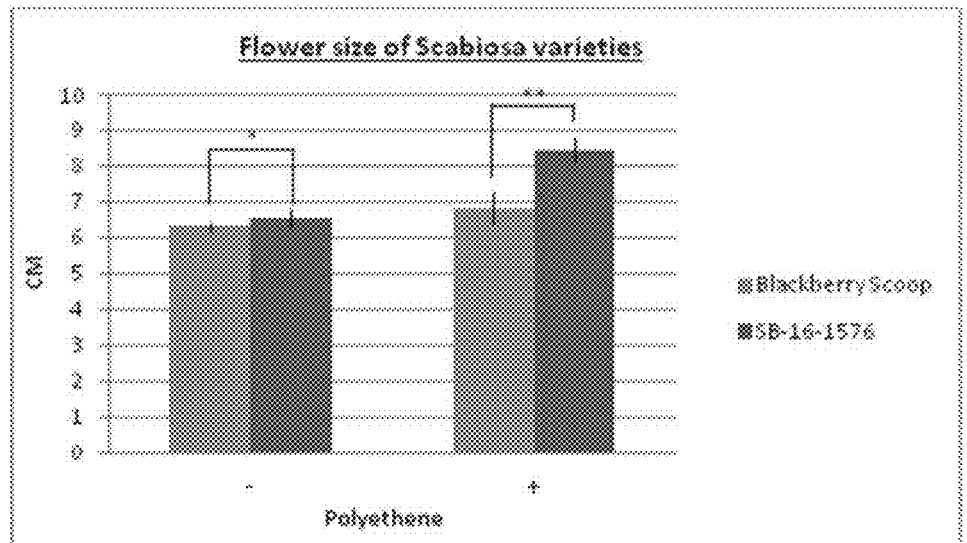
Figure 1D:
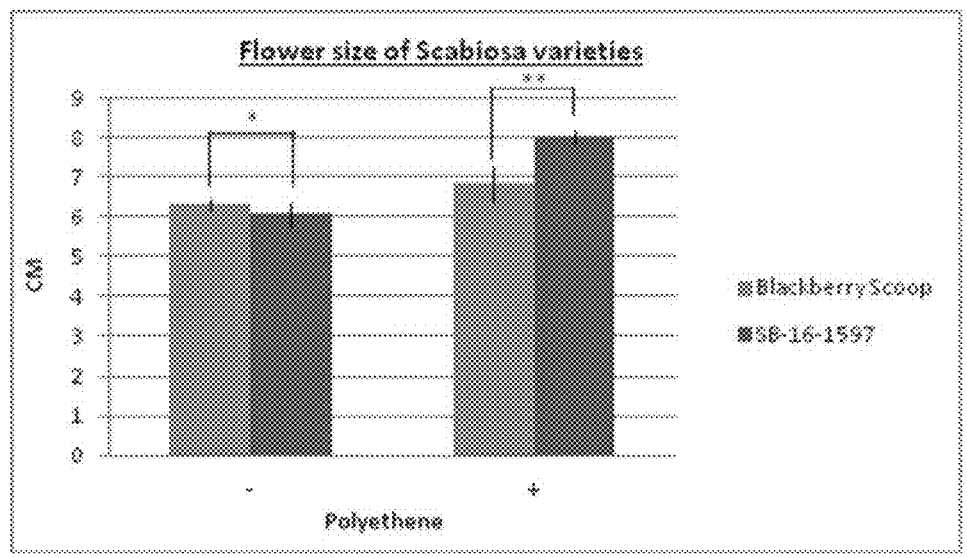
Figure 1E:
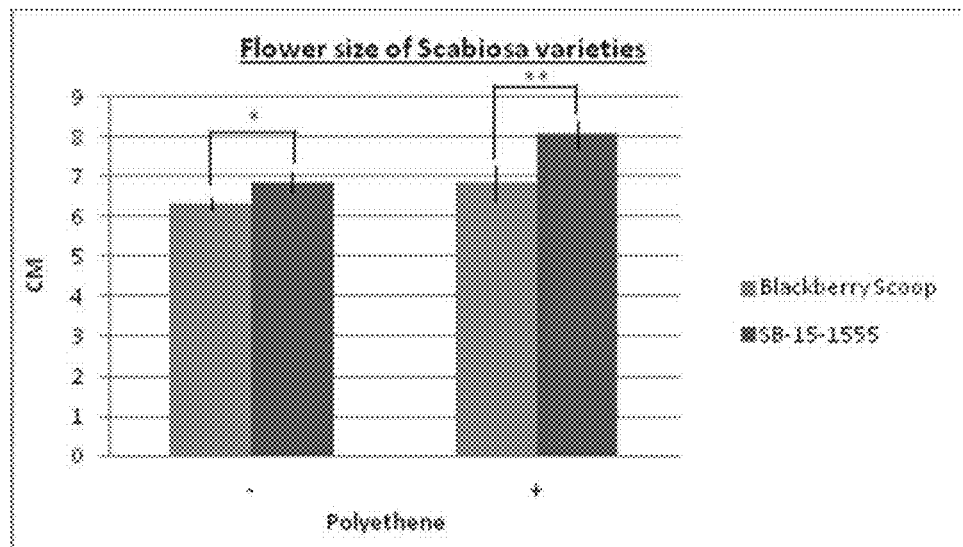
Figure 1F:
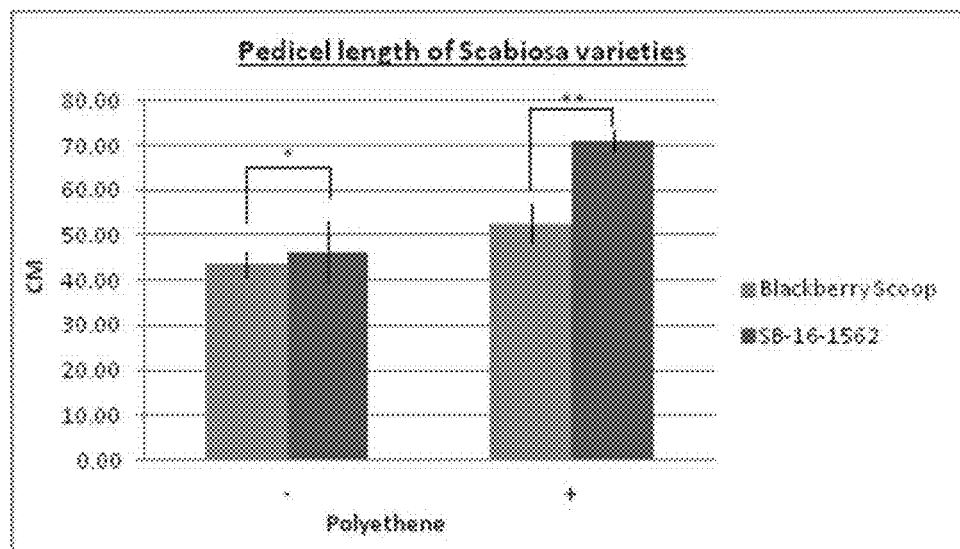
Figure 1G:
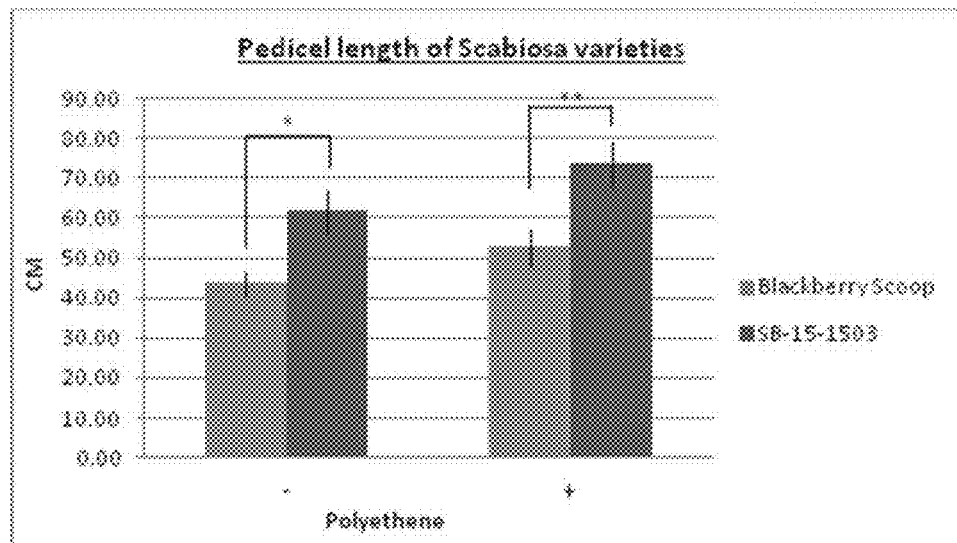
Figure 1H:
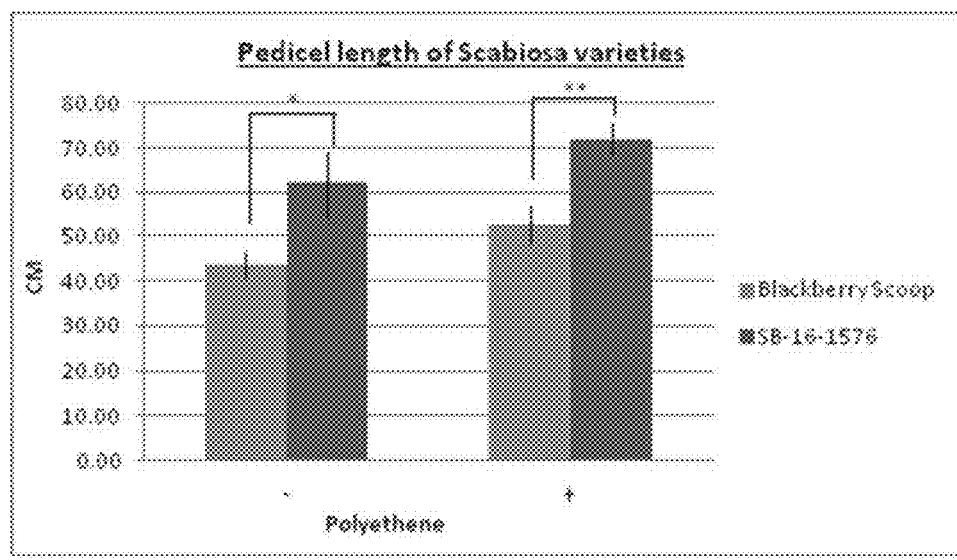
Figure 1I:
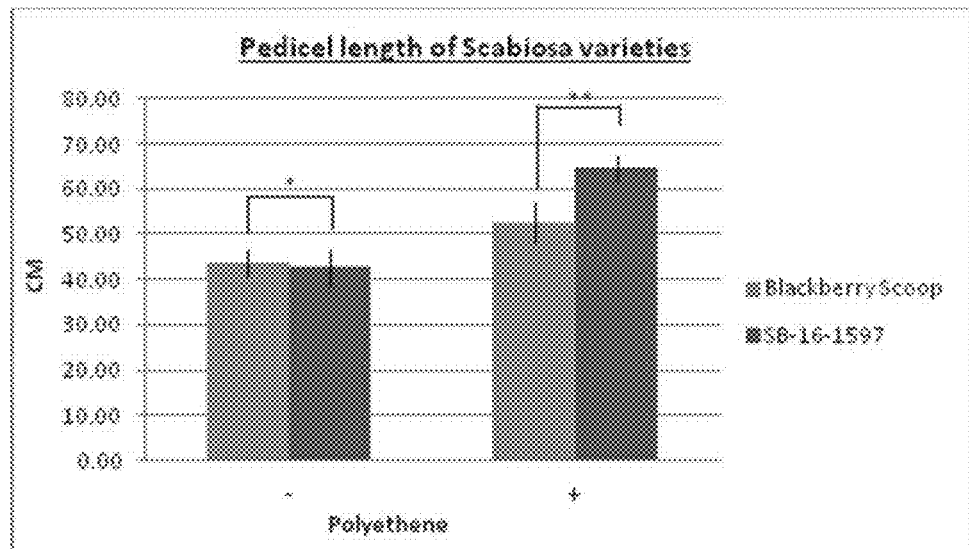
Figure 1J:
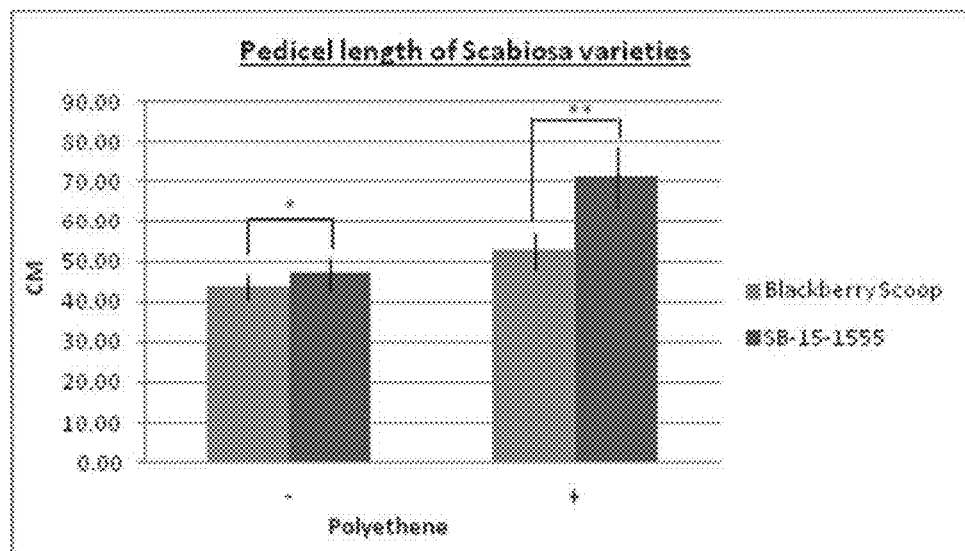
Figure 1K:
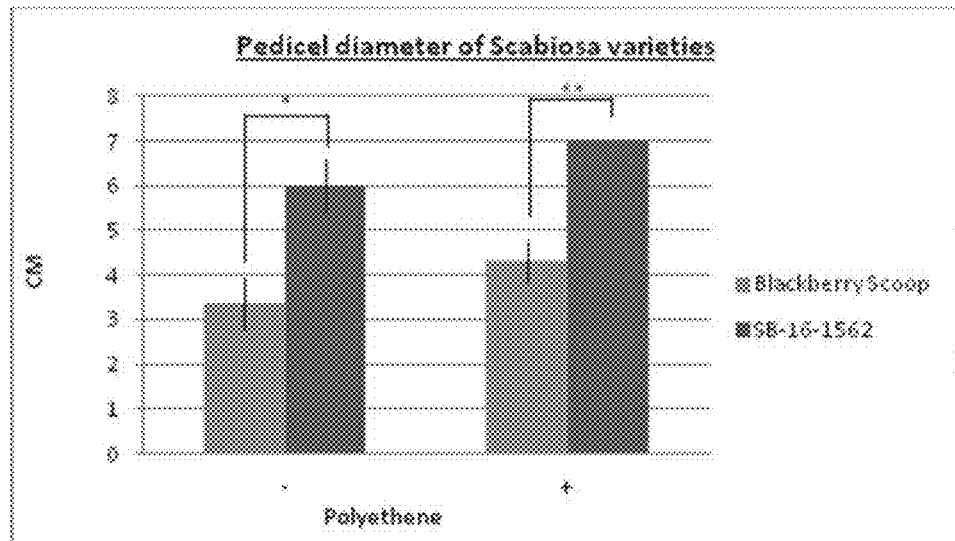
Figure 1L:
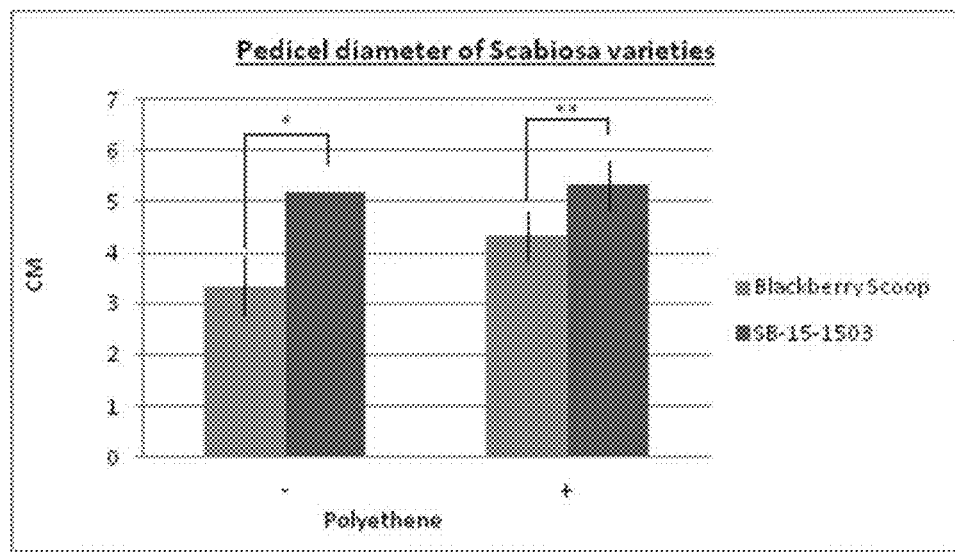
Figure 1M:
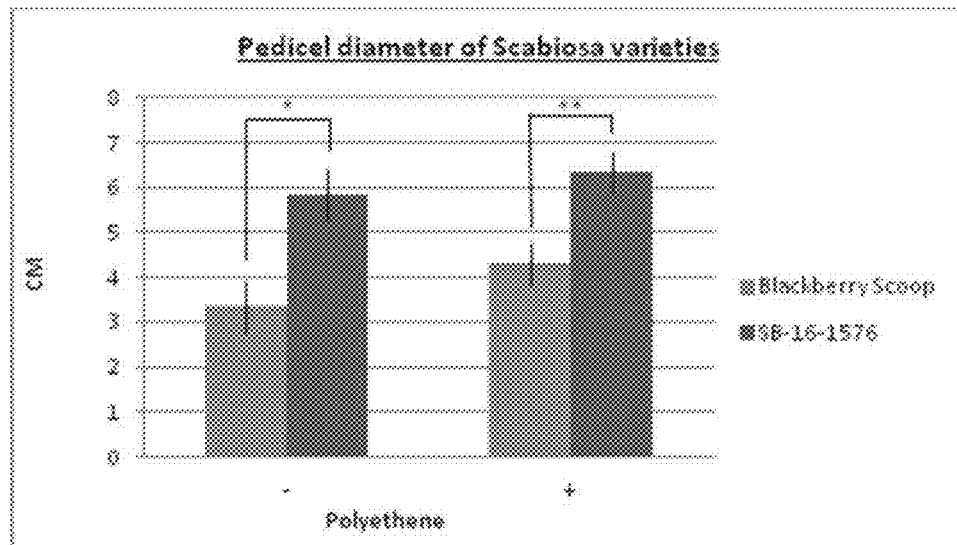
Figure 1N:
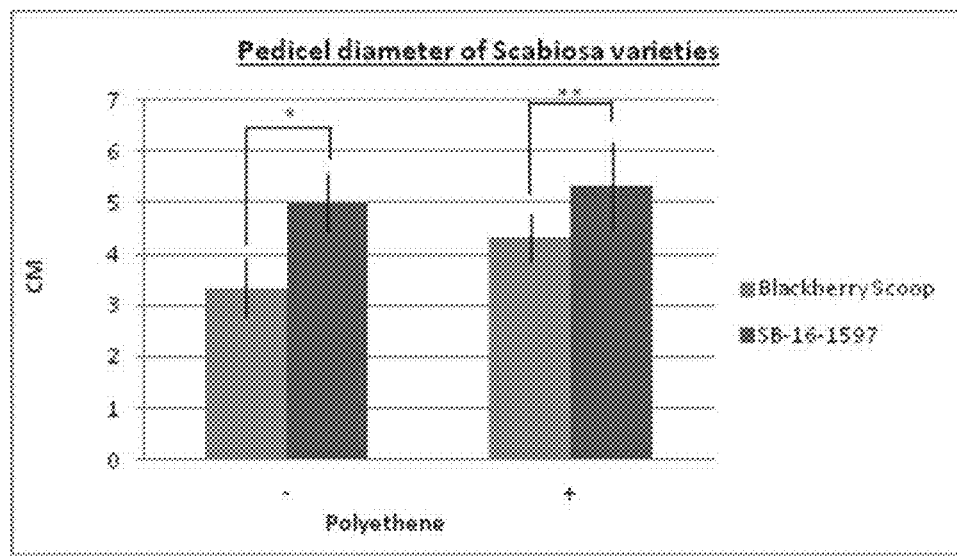
Figure 10:
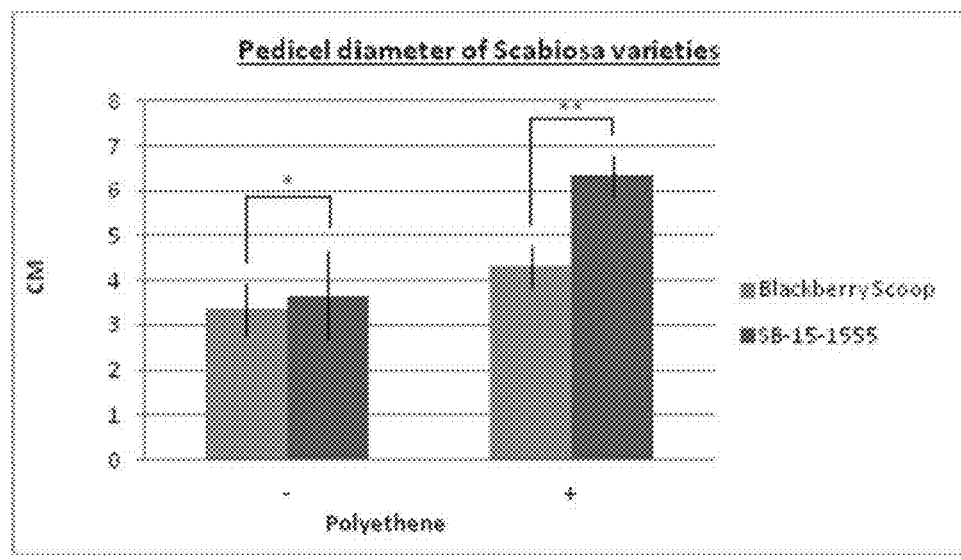

The present invention, in some embodiments thereof, relates to *Scabiosa atropurpurea* (*S. atropurpurea*) plants and methods of producing same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Endeavor to merge particular flower size and/or pedicel length and/or pedicel thickness traits with other desirable polygenic characteristics in *S. atropurpurea* have been excruciatingly slow and laborious. As described herein, however, the present inventors have devised a novel process for the induction and selection of *S. atropurpurea* plants having an unprecedented flower size, pedicel length, pedicel thickness or combinations thereof.

TERMINOLOGY

In the description which follows, a number of terms are used. In order to provide a clear and consistent understanding of the specification and claims, the following definitions are provided:

Line/genome/cultivar/variety—interchangeably used to refer to the genetic complement contained in the plant.

Maturity-refers to the full blossom of the inflorescence i.e., when the florets on the disc floret and ray floret are fully (maximally) open. Inflorescence can also be termed as a flower in this species, composed of ray and disc florets. All measures provided herein are at full maturity.

Inflorescence-refers to the assembly of florets (ray floret and disc floret) on a single pedicel.

Backcrossing—process in which a breeder repeatedly crosses hybrid progeny, for example a first generation hybrid (Fi), back to one of the parents of the hybrid progeny. Backcrossing can be used to introduce one or more single locus conversions from one genetic background into another.

Crossing—the mating of two parent plants.

Cross-pollination—fertilization by the union of two gametes from different plants (different genetic background).

Self-pollination: The transfer of pollen from the anther to the stigma of the same plant.

Hybrid—progeny of the cross of two non-isogenic plants.

Genotype—the genetic constitution of a cell or organism.

Phenotype—the detectable characteristics of a cell or organism, which characteristics are the manifestation of gene expression.

Pedigree breeding—a breeding technique that is used to create entirely new varieties of plants that combine the best qualities of selected existing varieties.

Plant height—plant height is taken from the top of soil to the top node of the plant and is measured in centimeters.

Substantially equivalent—a characteristic that, when compared, does not show a statistically significant difference (e.g., $p=0.05$) from the mean.

Thus, according to an aspect of the invention there is provided a *Scabiosa atropurpurea* plant characterized by an inflorescence diameter above 7 cm.

According to an aspect of the invention there is provided a *Scabiosa atropurpurea* plant characterized by a pedicel length above 60 cm.

According to an aspect of the invention there is provided a *Scabiosa atropurpurea* plant characterized by a pedicel diameter above 5 mm.

According to an aspect of the invention there is provided a *Scabiosa atropurpurea* plant characterized by a pedicel length above 60 cm and a pedicel diameter above 5 mm.

As used herein "*Scabiosa atropurpurea*" (and at time named for simplicity: "*Scabiosa*" but should not be confused with other *Scabiosa* species such as *S. columbaria*) also refers to mourningbride or sweet scabious, an ornamental plant of *Scabiosa* genus in the Caprifoliaceae family.

The plant can be of any color. Examples include, but are not limited to white (155A-155NND, 157A-159D), yellow (160A-163A, 1A-11-D), orange (12A-29D), pink (57NA-69D, 73A-74ND), red (33A-34N, 40A-56D, 57NA-69D), purple (70A-74ND), lavender75A-92NA) or green (154A-124A, e.g., SB-17-1635).

As used herein the term "plant" refers to a whole plant or parts thereof.

According to a specific embodiment, the plant is a hybrid plant (e.g., hybrid seed).

According to a specific embodiment, the plant is an inbred plant (e.g., inbred seed).

The phrase "plant part" refers to isolated plant cells or isolated plant parts (tissues) such as from which plants can be (re)generated, including plant protoplasts, plant cali, plant clumps, and plant cells that are intact in plants, or part of plants, such as pedicels, seeds, leaves, stems, pollens, roots, root tips, anthers, ovules, petals, flowers, florets, seedlings, embryos and bolls.

According to a specific embodiment the plant part is a flower.

According to a specific embodiment, the flower is a cut-flower.

According to a specific embodiment the plant part is a pollen.

According to a specific embodiment the plant part is an ovule.

According to a specific embodiment the plant part is a seed.

Also provided is a plant cutting (e.g., rooted or unrooted).

The plant may be of any *Scabiosa atropurpurea* varieties as long as it has the ability to develop large inflorescences (above 7 cm in diameter) under reduced radiation conditions as described hereinbelow.

*Scabiosa atropurpurea* varieties which can be used for developing plants of some embodiments of the invention are commercially available, such as of the Scoop series, developed by Danziger Dan Flower Farm, Israel.

Contemplated here a seed varieties and cuttings varieties.

Specific examples include, but are not limited to, Cherry Vanilla Scoop™ Blackberry Scoop™, Marshmallow Scoop™ or Vanilla Scoop™.

Additional examples include, but are not limited to, *scabiosa* by Hillverda (no series name known); as well as seed varieties, e.g., Imperial Giant™, Blue Cockade™, Black Night™, Snow Maiden™, Oxford Blue™, Beaujolias Bonnets™, Tall Double™ Series, Burgundy Beau™, QIS™ Series, Salmon Queen™.

As mentioned, according to some embodiments, the plant is characterized by an inflorescence diameter above 7 cm. Such a phenotype can be environmentally induced or genetic. Both parameters are contemplated herein.

According to some embodiments, the inflorescence measures refer to the first flowering inflorescence (flower). It will be appreciated that, as known to the skilled artisan, *Scabiosa* is characterized by a continuous flowering habit (about 3-6 months). It will be further appreciated that the plants of some embodiments of the invention are characterized by a continuous flowering period that is longer than that of their parents not subject to selection under reduced radiation conditions.

Inflorescence diameter can be determined visually using a ruler or a caliper.

Numbers provided herein are average per plant, per inflorescence or per population of plants of the same line.

As mentioned, the plant is characterized by an inflorescence diameter above 7 cm.

According to a specific embodiment the inflorescence diameter is between 7.1-10 cm.

According to a specific embodiment the inflorescence diameter is between 7.1-9.8 cm.

According to a specific embodiment the inflorescence diameter is between 7.5-10 cm.

According to a specific embodiment the inflorescence diameter is between 7.5-9.5 cm.

According to a specific embodiment the inflorescence diameter is between 8-10 cm.

According to a specific embodiment the inflorescence diameter is between 8-9 cm.

According to a specific embodiment the inflorescence diameter is between 8.3-10 cm.

According to a specific embodiment the inflorescence diameter is between 8-9.5 cm.

According to a specific embodiment the inflorescence diameter is above 7.3 cm.

According to a specific embodiment the inflorescence diameter is above 7.5 cm.

According to a specific embodiment the inflorescence diameter is above 7.8 cm.

According to a specific embodiment the inflorescence diameter is above 8 cm.

According to a specific embodiment the inflorescence diameter is above 8.2 cm.

According to a specific embodiment the inflorescence diameter is above 8.5 cm.

According to a specific embodiment the inflorescence diameter is above 8.7 cm.

According to a specific embodiment the inflorescence diameter is above 8.9 cm.

According to a specific embodiment, at least 10% (e.g., at least 15%, at least 30% e.g., at least 40%, e.g., at least 50%) of the inflorescences of the plant in a growth season are characterized by a diameter exceeding 7 cm.

According to a specific embodiment, the inflorescence refers to a first inflorescence on the plant.

According to a specific embodiment, the inflorescence refers to first 5 inflorescences produced.

The plants of the invention may have pedicel length and-or diameter which is about the same as that of the parent grown in the open (under natural radiation conditions without selection) or have a modified length and/or width. It will be appreciated that for large flowers, enlarged pedicels i.e., having increased length and diameter as compared to the parent may be advantageous in holding the inflorescence upright.

Thus, according to an embodiment, the plant is characterized by a pedicel length above 60 cm.

According to a specific embodiment, the plant is characterized by a pedicel length of 61-95 cm.

According to a specific embodiment, the plant is characterized by a pedicel length of 61-90 cm.

According to a specific embodiment, the plant is characterized by a pedicel length of 61-80 cm.

According to a specific embodiment, the plant is characterized by a pedicel length of 61-70 cm.

According to a specific embodiment, the plant is characterized by a pedicel length of 65-90 cm.

According to an additional or an alternative embodiment, the plant is characterized by a pedicel diameter above 5 mm.

According to a specific embodiment, the plant is characterized by a pedicel diameter of 5.1-10 mm.

According to a specific embodiment, the plant is characterized by a pedicel diameter of 5.1-9.5 mm.

According to a specific embodiment, the plant is characterized by a pedicel diameter of 5.1-9 mm.

According to a specific embodiment, the plant is characterized by a pedicel diameter of 5.1-8 mm.

According to a specific embodiment, the plant is characterized by a pedicel diameter of 5.1-7 mm.

According to a specific embodiment, the plant is characterized by a pedicel diameter of 5.1-6 mm.

According to a specific embodiment, the plant is characterized by the pedicel length and diameter of its ancestor e.g., pedicel length of 60 cm or lower and pedicel diameter of 5 mm or lower.

According to a specific embodiment, the plant is characterized by a pedicel length of 45-60 cm.

According to a specific embodiment, the plant is characterized by a pedicel length of 55-80 cm.

According to a specific embodiment, the plant is characterized by a pedicel length of 50-75 cm.

According to a specific embodiment, the plant is characterized by a pedicel length of 55-70 cm.

According to a specific embodiment, the inflorescence comprises a disc floret characterized by at least 90 florets.

According to a specific embodiment, the inflorescence comprises a disc floret characterized by at least 100 florets.

According to a specific embodiment, the inflorescence comprises a disc floret characterized by at least 110 florets.

According to a specific embodiment, the inflorescence comprises a disc floret characterized by at least 120 florets.

According to a specific embodiment, the inflorescence comprises a disc floret characterized by at least 130 florets.

According to a specific embodiment, the inflorescence comprises a disc floret characterized by at least 140 florets.

According to a specific embodiment, the inflorescence comprises a disc floret characterized by at least 150 florets.

According to a specific embodiment, the inflorescence comprises a disc floret characterized by at least 160 florets.

According to a specific embodiment, the inflorescence comprises a disc floret characterized by at least 170 florets.

According to a specific embodiment, the inflorescence comprises a disc floret characterized by at least 180 florets.

According to a specific embodiment, the inflorescence comprises a disc floret characterized by at least 190 florets.

According to a specific embodiment, the inflorescence comprises a disc floret characterized by at least 200 florets.

According to a specific embodiment, the inflorescence comprises a disc floret characterized by at least 210 florets.

According to a specific embodiment, the inflorescence comprises a disc floret characterized by at least 220 florets.

According to a specific embodiment, the inflorescence comprises a ray floret characterized by at least 33 florets.

According to a specific embodiment, the inflorescence comprises a ray floret characterized by at least 35 florets.

According to a specific embodiment, the inflorescence comprises a ray floret characterized by at least 40 florets.

According to a specific embodiment, the inflorescence comprises a ray floret characterized by at least 45 florets.

According to a specific embodiment, the inflorescence comprises a ray floret characterized by at least 50 florets.

According to a specific embodiment, the inflorescence comprises a ray floret characterized by at least 55 florets.

According to a specific embodiment, the inflorescence comprises a ray floret characterized by at least 5% increase in the number of florets as compared to that of the parent in the same developmental stage and control growth conditions As used herein "control growth condition" refer to growth in the absence of blockade of solar transmission and selection under these conditions as described herein but otherwise having the same abiotic and biotic conditions.

According to a specific embodiment, the inflorescence comprises a ray floret characterized by at least 10% increase in the number of florets as compared to that of the parent in the same developmental stage and control growth conditions.

According to a specific embodiment, the inflorescence comprises a ray floret characterized by at least 15% increase in the number of florets as compared to that of the parent in the same developmental stage and control growth conditions.

According to a specific embodiment, the inflorescence comprises a ray floret characterized by at least 20% increase in the number of florets as compared to that of the parent in the same developmental stage and control growth conditions.

According to a specific embodiment, the inflorescence comprises a ray floret characterized by at least 25% increase in the number of florets as compared to that of the parent in the same developmental stage and control growth conditions.

According to a specific embodiment, the inflorescence comprises a ray floret characterized by at least 30% increase in the number of florets as compared to that of the parent in the same developmental stage and control growth conditions.

According to a specific embodiment, the inflorescence comprises a ray floret characterized by at least 40% increase in the number of florets as compared to that of the parent in the same developmental stage and control growth conditions.

According to a specific embodiment, the inflorescence comprises a ray floret characterized by at least 50% increase in the number of florets as compared to that of the parent in the same developmental stage and control growth conditions.

According to a specific embodiment, the inflorescence comprises a ray floret characterized by at least 60% increase in the number of florets as compared to that of the parent in the same developmental stage and control growth conditions.

According to a specific embodiment, the inflorescence comprises a ray floret characterized by at least 70% increase in the number of florets as compared to that of the parent in the same developmental stage and control growth conditions.

According to a specific embodiment, the inflorescence comprises a ray floret characterized by at least 80% increase in the number of florets as compared to that of the parent in the same developmental stage and control growth conditions.

According to a specific embodiment, the inflorescence comprises a ray floret characterized by at least 90% increase in the number of florets as compared to that of the parent in the same developmental stage and control growth conditions.

According to a specific embodiment, the inflorescence comprises a ray floret characterized by at least 100% increase in the number of florets as compared to that of the parent in the same developmental stage and control growth conditions.

As used herein "control growth conditions" means identical conditions only under natural light/radiation e.g., not covered by a polythene sheet.

According to a specific embodiment, the inflorescence comprises a disc floret characterized by at least 5% increase in the number of florets as compared to that of the parent in the same developmental stage and control growth conditions.

According to a specific embodiment, the inflorescence comprises a disc floret characterized by at least 5% increase in the number of florets as compared to that of the parent in the same developmental stage and control growth conditions.

According to a specific embodiment, the inflorescence comprises a disc floret characterized by at least 10% increase in the number of florets as compared to that of the parent in the same developmental stage and control growth conditions.

According to a specific embodiment, the inflorescence comprises a disc floret characterized by at least 20% increase in the number of florets as compared to that of the parent in the same developmental stage and control growth conditions.

According to a specific embodiment, the inflorescence comprises a disc floret characterized by at least 30% increase in the number of florets as compared to that of the parent in the same developmental stage and control growth conditions.

According to a specific embodiment, the inflorescence comprises a disc floret characterized by at least 40% increase in the number of florets as compared to that of the parent in the same developmental stage and control growth conditions.

According to a specific embodiment, the inflorescence comprises a disc floret characterized by at least 50% increase in the number of florets as compared to that of the parent in the same developmental stage and control growth conditions.

According to a specific embodiment, the inflorescence comprises a disc floret characterized by at least 60% increase in the number of florets as compared to that of the parent in the same developmental stage and control growth conditions.

According to a specific embodiment, the inflorescence comprises a disc floret characterized by at least 70% increase in the number of florets as compared to that of the parent in the same developmental stage and control growth conditions.

According to a specific embodiment, the inflorescence comprises a disc floret characterized by at least 80% increase in the number of florets as compared to that of the parent in the same developmental stage and control growth conditions.

According to a specific embodiment, the inflorescence comprises a disc floret characterized by at least 90% increase in the number of florets as compared to that of the parent in the same developmental stage and control growth conditions.

According to a specific embodiment, the inflorescence comprises a disc floret characterized by at least 100% increase in the number of florets as compared to that of the parent in the same developmental stage and control growth conditions.

According to a specific embodiment, the inflorescence comprises a disc floret characterized by at least 110% increase in the number of florets as compared to that of the parent in the same developmental stage and control growth conditions.

According to a specific embodiment, the inflorescence comprises a disc floret characterized by at least 120% increase in the number of florets as compared to that of the parent in the same developmental stage and control growth conditions.

According to a specific embodiment, the inflorescence comprises a disc floret characterized by at least 130% increase in the number of florets as compared to that of the parent in the same developmental stage and control growth conditions.

According to a specific embodiment, the inflorescence comprises a disc floret characterized by at least 150% increase in the number of florets as compared to that of the parent in the same developmental stage and control growth conditions.

According to a specific embodiment, the inflorescence comprises a disc floret characterized by at least 170% increase in the number of florets as compared to that of the parent in the same developmental stage and control growth conditions.

According to a specific embodiment, the inflorescence comprises a disc floret characterized by at least 190% increase in the number of florets as compared to that of the parent in the same developmental stage and control growth conditions.

According to a specific embodiment, the inflorescence comprises a disc floret characterized by at least 200% increase in the number of florets as compared to that of the parent in the same developmental stage and control growth conditions.

According to a specific embodiment, the inflorescence comprises a disc floret characterized by at least 220% increase in the number of florets as compared to that of the parent in the same developmental stage and control growth conditions.

According to a specific embodiment, the inflorescence comprises a disc floret characterized by at least 240% increase in the number of florets as compared to that of the parent in the same developmental stage and control growth conditions.

According to a specific embodiment, the inflorescence comprises a disc floret characterized by at least 260% increase in the number of florets as compared to that of the parent in the same developmental stage and control growth conditions.

According to a specific embodiment, the inflorescence comprises a disc floret characterized by at least 280% increase in the number of florets as compared to that of the parent in the same developmental stage and control growth conditions.

According to a specific embodiment, the inflorescence comprises a disc floret characterized by at least 300% increase in the number of florets as compared to that of the parent in the same developmental stage and control growth conditions.

According to a specific embodiment, the inflorescence comprises a disc floret and ray floret numbers higher that of the parent in the same developmental stage and control growth conditions.

According to a specific embodiment, the inflorescence comprises ray florets that are at least 23 mm long and disc florets are at least 12 mm long.

According to a specific embodiment, the disc florets and ray florets are of the same dimension as those of the parent in the same developmental stage and control growth conditions.

According to a specific embodiment, the inflorescence is green due to the presence of receptacular bracts (chaff) (smaller florets with receptacular bracts that are longer than that of the parent not subject to growth/selection under reduced solar radiation as described herein). An exemplary line is SB-17-1635, seeds of which having been deposited under the Budapest treaty at the NCIMB Ltd. (Ferguson Building Craibstone Estate, Bucksburn. Aberdeen Scotland) under NCIMB43102 on Jul. 11, 2018.

According to specific embodiments, anthesis of florets of a disc floret of the inflorescence occurs 2-3 days (e.g., 3 days) following anthesis of florets of a ray floret of the inflorescence. Such an inflorescence has a scoop-like-appearance and is typically characterizing inflorescence of the parent not subject to growth/selection under reduced solar radiation as described herein).

According to another specific embodiment, anthesis of florets of a disc floret of the inflorescence and anthesis of florets of a ray floret of the inflorescence occurs simultaneously (i.e., less than 48 hours interval in anthesis).

Exemplary lines characterized by a ball shape include, but are not limited to SB-16-1539 and SB-16-1589.

Such an inflorescence has a ball-like appearance and hence is also referred to as "full-flower" or "ball shape".

Examples of plant varieties which are characterized by inflorescence diameter above 7 cm is provided in SB-15-1483, seeds of which having been deposited under the Budapest Treaty at the Korean Collection for Type Cultures under KCTC13541BP on Jun. 5, 2018; SB-15-1484, seeds of which having been deposited under the Budapest treaty at the NCIMB Ltd. (Ferguson Building Craibstone Estate, Bucksburn. Aberdeen Scotland) under NCIMB43095 on Jul. 11, 2018; SB-15-1503, seeds of which having been deposited under the Budapest treaty at the NCIMB Ltd. (Ferguson Building Craibstone Estate, Bucksburn. Aberdeen Scotland) under NCIMB43096 on Jul. 11, 2018; SB-15-1504, seeds of which having been deposited under the Budapest Treaty at the Korean Collection for Type Cultures under KCTC13542BP on Jun. 5, 2018; SB-15-1577, seeds of which having been deposited under the Budapest treaty at the NCIMB Ltd. (Ferguson Building Craibstone Estate, Bucksburn. Aberdeen Scotland) under NCIMB43141 on Aug. 6, 2018; SB-16-1593, seeds of which having been deposited under the Budapest treaty at the NCIMB Ltd. (Ferguson Building Craibstone Estate, Bucksburn. Aberdeen Scotland) under NCIMB43139 on Jul. 11, 2018; SB-16-1597, seeds of which having been deposited under the Budapest treaty at the NCIMB Ltd. (Ferguson Building Craibstone Estate, Bucksburn. Aberdeen Scotland) under NCIMB43142 on Aug. 6, 2018; SB-15-1575, seeds of which having been deposited under the Budapest treaty at the NCIMB Ltd. (Ferguson Building Craibstone Estate, Bucksburn. Aberdeen Scotland) under NCIMB43138 on Jul. 11, 2018; SB-15-1574, seeds of which having been deposited under the Budapest treaty at the NCIMB Ltd. (Ferguson Building Craibstone Estate, Bucksburn. Aberdeen Scotland) under NCIMB43140 on Aug. 6, 2018; SB-15-1550, seeds of which having been deposited under the Budapest Treaty at the Korean Collection for Type Cultures under KCTC13543BP on Jun. 5, 2018; SB-15-1592, seeds of which having been deposited under the Budapest Treaty at the Korean Collection for Type Cultures under KCTC13545BP on Jun. 5, 2018; SB-16-1539, seeds of which having been deposited under the Budapest treaty at the NCIMB Ltd. (Ferguson Building Craibstone Estate, Bucksburn. Aberdeen Scotland) under NCIMB43099 on Jul. 11, 2018; SB-16-1576, seeds of which having been deposited under the Budapest Treaty at the Korean Collection for Type Cultures under KCTC13547BP on Jun. 5, 2018; SB-15-1496, seeds of which having been deposited under the Budapest treaty at the NCIMB Ltd. (Ferguson Building Craibstone Estate, Bucksburn. Aberdeen Scotland) under NCIMB43070 on Jun. 5, 2018; SB-16-1528, seeds of which having been deposited under the Budapest treaty at the NCIMB Ltd. (Ferguson Building Craibstone Estate, Bucksburn. Aberdeen Scotland) under NCIMB43071 on Jun. 5, 2018; SB-15-1515, seeds of which having been deposited under the Budapest treaty at the NCIMB Ltd. (Ferguson Building Craibstone Estate, Bucksburn. Aberdeen Scotland) under NCIMB43097, on Jul. 11, 2018; SB-16-1555, seeds of which having been deposited under the Budapest treaty at the NCIMB Ltd. (Ferguson Building Craibstone Estate, Bucksburn. Aberdeen Scotland) under NCIMB43100, on Jul. 11, 2018; SB-16-1562, seeds of which having been deposited under the Budapest treaty at the NCIMB Ltd. (Ferguson Building Craibstone Estate, Bucksburn. Aberdeen Scotland) under NCIMB43101, on Jul. 11, 2018. As mentioned, the *Scabiosa* plants of some embodiments of the invention are obtainable by growing the plants under reduced radiation conditions.

Thus, according to an aspect of the invention, there is provided a method of developing a *Scabiosa* plant as described herein, the method comprising:
  (a) growing *Scabiosa atropurpurea* plants under a cover to result in reduced solar radiation conditions; and
  (b) selecting a plant of said plants that exhibits an inflorescence having a larger diameter, pedicel length and/or pedicel diameter than that of said *Scabiosa atropurpurea* plants in the same developmental stage and control growth conditions.

According to a specific embodiment, the method further comprises selfing or crossing said plant or plants and selecting for said inflorescence having said larger diameter, pedicel length and/or pedicel diameter.

*Scabiosa* varieties for cut flowers are harvested continuously for 3-6 months (period depends on climate) starting at the beginning of the flowering period.

First flowers produced by a *Scabiosa* plant in the flowering period tend to be the largest and are also characterized with the longest and thickest pedicels compared to later periods in the flowering season. The reason for that is that once a pedicel harvested two dormant buds below it is induced for flowering. This results in a logarithmic increase in active buds and flowers the plant carries through the flowering season. An outcome of this increase may be morphological changes in flowers and pedicles: pedicels grow shorter and thinner and flowers smaller respectively as flowering season is going forward.

As used herein "reduced solar radiation conditions" refers to reduced solar radiation as compared to the solar radiation under the same conditions without a film coverage or any other artificial means aimed at reducing the solar radiation.

Thus, according to some embodiments, the plants are grown in a tunnel (e.g., low tunnel) or greenhouse.

The horticultural growth of *Scabiosa* is well within the skills of the artisan. Accordingly, the plants are grown under standard temperature and irrigation regimen, with the necessary modifications arising from growth under a film cover.

According to a specific embodiment, growing is under a temperature not exceeding 25° C.

According to a specific embodiment, the plants are sown or planted in the ground, pots or beds. For example the seeds are sown in planters, transplanted to plugs and then planted in the soil.

According to some embodiments, the sown seeds or plantlets are covered with a synthetic film, e.g., plastic.

According to a specific embodiment, the cover is applied throughout the life time of the plant. According to another embodiment, the cover is applied only during the flowering induction stage.

According to another embodiment, the cover is applied at least during the flowering induction stage.

According to a specific embodiment, reduced radiation conditions as described herein is part of the instructions to the growers.

Film covers are widely used for cultivation (but have not been used to date for the cultivation of *Scabiosa atropurpurea*). Film sizes depend on the type and dimensions of the structure.

According to a specific embodiment, film width typically up to 16 meters, while the thickness is typically to 120 µm.

According to a specific embodiment, the film is selected having a desired thermo, optical and mechanical properties. The film may also have additional features such as anti-drip, anti-dust, anti-virus, anti-mist and/or anti-fog.

Solar radiation is the radiation that comes from the sun in the form of electromagnetic waves that cover the spectrum ranging from 0.2 to 2.5 µm. In particular the solar radiation is constituted of UV rays, visible region (Vis) and an infrared (IR) part.

According to a specific embodiment, the film is characterized by blockade of UV-A (e.g., complete blockade, 100%).

According to a specific embodiment, the film is characterized by blockade of UV-A and UV-B.

According to a specific embodiment, the film is characterized by a complete cut of UV radiation (100%) or that is partially transmissible (at least 50%, 50-100%, 70-100%, 80-100%, 90-100%).

According to a specific embodiment, the reduced radiation conditions comprise no transmission of UV (300-380 nm), 90% transmission of PAR (400-700 nm) diffused.

Measures are taken to select a sheet (film) that still allows light transmission that supports plant growth and development. Light measurements can be done using a spectrophotometer.

By interfering with the effect of the solar energy on the plant, the cover is considered photo-selective.

According to a specific embodiment, the greenhouse or tunnel is covered by a polyethene film.

According to a specific embodiment, the polyethene sheet has substantially the same specification as that of "SUN-SELECTOR" AV thermal IR, C400 IR AV DIFF-120 micron, Genigar, Israel).

According to a specific embodiment, the reduced radiation is at least 40% reduction in the solar radiation out of said greenhouse.

Once a plant having the desired inflorescence is obtained it can be subject to selfing or crossing and selecting for the inflorescence having the larger diameter, pedicel length and/or pedicel diameter. This may help in stabilizing the phenotype in future generations and improve it (increasing the inflorescence).

Thus, according to an embodiment there is provide a *Scabiosa atropurpurea* plant obtainable according to the method as described herein.

Also provided is a method of producing a *Scabiosa atropurpurea* plant, the method comprising:
(a) crossing the plant having the inflorescence as described herein with another *Scabiosa atropurpurea* plant as described herein, wherein the plant and another plant are of different genetic backgrounds;
(b) recovering seeds following the crossing;
(c) planting the seeds and growing the seed into plants; and
(d) selecting a hybrid plant.

According to a specific embodiment, the selecting is according to inflorescence diameter and/or pedicel length and diameter.

According to a specific embodiment, the selecting is according to inflorescence diameter.

Also provided here is a hybrid plant or part thereof produced as described herein.

According to an aspect there is provided a method of developing a cultivated plant using plant breeding techniques, the method comprising using the plant or plant part as described herein as a source of breeding material for self-breeding and/or cross-breeding.

Seeds of the plants of the present invention may be seeded and therefore the present invention contemplates a sawn field. Vegetative portions of the plants of the invention can be planted. Thus the present invention also contemplates a planted field or a potted plant.

The plant cutting can be placed in a container (such as a growth cell, a plug) which contains the plant cutting and therefore the present invention also contemplates the holding vessel which comprises the cuttings. The plant cutting may be rooted or unrooted.

The cut flowers can be placed in a container (such as a vase, a bucket or pail or another holding apparatus) which contains the cut flowers and therefore the present invention also contemplates the holding vessel which comprises the cuttings.

The plants of the invention can also be rooted, grown or held in a container with other plant species (such as having at least one growth characteristic e.g., rooting time, growth rate) for the display of single species or multispecies combinations (also referred to in the art as combos, Mixies™, Trixies™ and the like). Such configurations are taught for example in U.S. Pat. No. 8,136,294, which is hereby incorporated by reference in its entirety.

It is expected that during the life of a patent maturing from this application many relevant *S. atropurpurea* will be developed and the scope of the term *S. atropurpurea* is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Experimental Procedures and Results

Seedlings of *Scabiosa atropurpurea* were grown in a tunnel covered with a polyethylene sheet (Genigar, Israel: "SUN-SELECTOR" AV thermal IR, C400 IR AV DIFF-120 micron) instead of being grown outside in the open field as commonly done.

It was found that a portion of the lines showed a set of new features under polyethethylene films: flower size is larger and pedicels are longer and thicker compared to open field in this portion of varieties, changes in flower morphology under polyethylene films were characterized also by an increase in ray and disc floret quantities (see Table 2). The main morphological cause for larger flowers development under polyethethylene films are the higher quantities of flowers in both ray and disc florets. Once those flowers develop and open a phenotype of larger flowers can be observed.

Disc floret quantities show the strongest response to climate conditions with an increase of up to 234% in quantity per single receptacle. Ray floret also show a moderate increase in quantity per single receptacle of up to 67% (see Table 2).

TABLE 2

Growing climates effect on number of florets per receptacle
Describes the mean number of florets in the ray or disc floret (as was measured in 10 flowers of each variety) of 5 different commercial Scabiosa varieties under two different climate conditions:
(+) with polyethylene cover-Green house or (−) without polyethylene cover - Open field.
The ratio between floret number in either ray or disc floret was calculated as:

$$\frac{\text{number of flowers }(+)}{\text{number of flowers }(-)} \times 100\%$$

| | | Cherry Vanilla Scoop ™ | | Blackberry Scoop ™ | | Marshmellow Scoop ™ | | Vanilla Scoop ™ | |
|---|---|---|---|---|---|---|---|---|---|
| Variety Polyethene | | + | − | + | − | + | − | + | − |
| Ray Floret | Number of flowers | 35.75 | 32 | 34.6 | 24.6 | 40.6 | 24.3 | 41 | 31 |
| | Ratio of flowers (+/−) | 111.72% | | 140.65% | | 167.08% | | 132.26% | |
| Disc Floret | Number of flowers | 112.5 | 76 | 125 | 87.6 | 130 | 61 | 156 | 66.7 |
| | Ratio of flowers (+/−) | 148.03% | | 142.69% | | 213.11% | | 233.88% | |

As a Result of Growing Under Polyethethylene Sheet the Ultraviolet (UV) Radiation Reduced substantially by at least 50% (the values in Table 1 are of the PAR (400-700 nm) (See Table 1)), which resulted in flower development under novel climate conditions of non-UV (100% blockade) and 50% of the PAR radiation. This in turn led the varieties to exhibit bigger flowers and longer and thicker pedicels.

TABLE 1

Radiation comparison (PAR)

| Open field-No cover | Greenhouse-polyethylene cover |
|---|---|
| 46500 | 23100 |

Table 1: Describes a single radiation measurement taken on November 2016, Nir-Zvi, Israel with or without the polyethene cover. Measurement are provided in LUX.

In order to show the radiation effect on flowers and pedicel characteristics, the following commercial varieties Cherry Vanilla Scoop™, Blackberry Scoop™, Marshmallow Scoop™ and Vanilla Scoop™ were compared under the two growth regimes while measuring: flower size, pedicel length and pedicel diameter.

An increase in floret number under polyethylene cover was also observed in the selected large floret lines. The major difference in floret number was within the ray floret.

TABLE 2a

| Ratio of florets (+/−) | Total Floret number | Ray floret | Disc floret |
|---|---|---|---|
| SB-15-1504 | 170.90% | 149.07% | 182.51% |
| SB-16-1528 | 130.36% | 145.20% | 125.96% |
| SB-15-1496 | 100.66% | 161.82% | 90.96% |
| SB-16-1550 | 107.69% | 177.91% | 90.24% |
| SB-16-1562 | 109.86% | 198.69% | 107.96% |
| SB-16-1575 | 124.41% | 185.02% | 99.67% |
| SB-15-1503 | 129.18% | 207.10% | 110.99% |
| SB-16-1592 | 138.91% | 153.96% | 135.86% |
| SB-15-1483 | 124.70% | 151.58% | 114.02% |
| SB-16-1576 | 132.66% | 155.60% | 140.17% |
| SB-17-1635 | 113.32% | 144.62% | 101.61% |
| SB-15-1484 | 130.67% | 157.14% | 120.40% |
| SB-16-1577 | 119.60% | 216.18% | 89.20% |
| SB-16-1597 | 91.15% | 114.91% | 83.75% |
| SB-16-1555 | 149.73% | 109.95% | 163.87% |
| SB-16-1574 | 140.40% | 174.40% | 127.00% |
| Blackberry Scoop | 140.98% | 143.28% | 140.27% |

TABLE 3

| Hour | | 06:00 | | 12:00 | | 18:00 | | 00:00 | |
|---|---|---|---|---|---|---|---|---|---|
| | Location | Out | In | Out | In | Out | In | Out | In |
| Radiation (LUX) | Min | −2,527 | −151 | 50,747 | 3,045 | 13,369 | 924 | −2,322 | −154 |
| | Max | 7,786 | 1,178 | 475,504 | 298,539 | 395,184 | 235,993 | 1,503 | 1,280 |
| | Avr | 497 | −23 | 263,472 | 18,798 | 208,672 | 13,963 | −1,483 | −87 |

The selected lines which generated the desired response under the new conditions were selfed/crossed to create a novel germpalsm characterized by substantially larger flowers and/or longer pedicels and/or bigger pedicels as compared to normal radiation (without the cover). These lines were stabilized for the above mentioned traits. Table 4 below provides phenotypic description for these lines.

TABLE 4

Characteristics of different genetic backgrounds (at maturity)

| Mean (SD) | Flower Size (cm) | | Pedicel length (cm) | | Pedicel diameter (cm) | | Deposit | |
|---|---|---|---|---|---|---|---|---|
| polyethene | − | + | − | + | − | + | No. | Description |
| SB-15-1504 | 5.94 (0.26) | 8.24 (0.26) | 61.67 (2.52) | 78.67 (3.51) | 4.51 (0.58) | 5.33 (0.69) | KCTC13542BP | Flower color-Lavender |
| SB-16-1528 | 6.18 (0.22) | 8.26 (0.29) | 65.00 (4.36) | 62.00 (5.00) | 5.12 (0.58) | 5.33 (0.83) | NCIMB43071 | Flower color-purple |
| SB-15-1496 | 6.08 (0.13) | 8.84 (0.05) | 69.33 (2.52) | 71.33 (8.02) | 5.17 (0.58) | 7.33 (0.69) | NCIMB43070 | Flower color-Dark pink |
| SB-16-1550 | 7.30 (0.10) | 8.48 (0.28) | 66.67 (4.51) | 69.00 (5.00) | 4.84 (0) | 5.67 (0.47) | KCTC13543BP | Flower color-White |
| SB-16-1562 | 6.56 (0.40) | 8.14 (0.33) | 46.33 (7.02) | 71.00 (2.65) | 6.01 (0.58) | 7.00 (0.00) | NCIMB43101 | Flower color-Red |
| SB-16-1575 | 7.52 (0.43) | 8.90 (0.21) | 57.33 (6.66) | 76.67 (4.51) | 5.89 (0.58) | 6.67 (0.47) | NCIMB43138 | Flower color-White |
| SB-15-1503 | 6.32 (0.26) | 8.00 (0.14) | 61.67 (5.51) | 73.67 (5.69) | 5.17 (0.00) | 5.33 (0.47) | NCIMB43096 | Flower color-Lavender |
| SB-16-1592 | 6.40 (0.31) | 8.08 (0.31) | 59.67 (6.81) | 63.00 (5.57) | 6.27 (0.00) | 6.67 (0.47) | KCTC13545BP | Flower color-Dark Purple |
| SB-15-1483 | 6.3 (0.31) | 7.86 (0.24) | 60.00 (5.29) | 63.33 (5.69) | 5.43 (0.58) | 6.00 (0.00) | KCTC13541BP | Flower color-Lavender |
| SB-16-1576 | 6.54 (0.25) | 8.46 (0.34) | 62.00 (7.55) | 72.00 (3.61) | 5.85 (0.58) | 6.33 (0.47) | KCTC13547BP | Flower color-White |
| SB-17-1635 | 6.48 (0.23) | 8.08 (0.47) | 62.33 (4.51) | 64.33 (7.09) | 4.84 (0.58) | 5.67 (0.58) | | Flower color-Dark Bordeaux |
| SB-15-1484 | 6.24 (0.18) | 6.72 (0.43) | 57.67 (5.13) | 46.00 (3.61) | 4.71 (0.58) | 5.33 (0.47) | | Flower color-Lavender |
| SB-16-1577 | 7.28 (0.16) | 8.72 (0.42) | 52.67 (4.04) | 68.67 (5.51) | 4.35 (0.58) | 6.67 (0.47) | NCIMB43141 | Flower color-White |
| SB-16-1597 | 6.06 (0.32) | 8.00 (0.19) | 42.67 (4.04) | 64.67 (3.06) | 5.01 (0.58) | 5.33 (0.83) | NCIMB43142 | Flower color-White |
| SB-16-1555 | 6.85 (0.26) | 8.06 (0.36) | 47.00 (4.00) | 71.3 (7.51) | 3.67 (1.00) | 6.33 (0.47) | NCIMB43100 | Flower color-Pink |
| SB-16-1574 | 7.44 (0.33) | 8.48 (0.40) | 52.00 (2.65) | 73.00 (4.00) | 3.88 (0.58) | 7.00 (0.00) | NCIMB43140 | Flower color-White |
| Blackberry scoop | 6.32 (0.13) | 6.82 (0.45) | 43.67 (3.06) | 52.67 (4.51) | 3.35 (0.58) | 4.33 (0.47) | | Flower color-Black |
| All large flower varieties | 6.63 (0.49) | 8.11 (0.57) | 38.12 (5.26) | 65.68 (9.40) | 5.00 (0.69) | 6.02 (0.63) | | |

FIGS. 1A-O show the changes in characteristics in response to polyethylene covering. Blackberry scoop, a commercially available variety, was used as control. This variety is characterized by flowers which are less than 5 cm in diameter at maturity and pedicles which are less then 45 cm long and 3.5 cm in diameter. T test was conducted to determine the statistical significance of the differences between the large flowers obtained according to some embodiments of the invention versus control. Differences are statistically significant only under polyethene cover, *P value>0.02**P value<0.02.

Genetic Background 1:

Lavender Scoop™ was grown in a tunnel structure under polyethethylene films during the Israeli winter season of 2012. Under these conditions a *scabiosa* plant with slightly bigger (7 cm as compared to 6 cm-normally featuring this variety under normal radiation i.e., not covered) flowers. This plant was subject to self-pollinations. Growth and selection were done under reduced radiation (polyethylene sheets as described above).

A population of approximately 1000 seeds was derived from self pollinations of this plant between 2013 to 2015.

The progeny seeds were sown and out of them 700 plants were grown in the tunnel for observations and selections for flower size and/or pedicel length and/or pedicel thickness, resulting in 4 lines (1484, 1483, 1503, 1504) which displayed big flowers and/or long pedicels and/or thick pedicels. 1483, 1503, 1504 are varieties with long and thick pedicels and big flowers. 1484 is a variety with big flowers and long pedicels.

During 2016, the variety 1503 was planted in the greenhouse and subjected to self pollinations. Growth and selection were done under reduced radiation (polyethylene sheets as described above).

A population of approximately 300 seeds was derived from self pollinations of this plant during 2016. The progeny seeds were sown and out of them 200 plants were grown in the tunnel for observations and selections for flower size and/or pedicel length and/or pedicel thickness and/or ball shape and/or receptacular bracts (chaff) length, resulting in 3 lines (1539, 1589, 1635) with displayed flower size and/or pedicel length and/or pedicel thickness and/or flower type (ball shape) and/or receptacular bracts (chaff) length. 1539, 1589 are varieties with ball shape flower (ball shape), big flower, long and thick pedicels. 1635 is a variety with longer receptacular bracts (Chaff).

Genetic Background 2:

The inventor found a *Scabiosa atropurpurea* plant (of the 1423 background) with slightly bigger flowers (8 cm as compared to 6 cm-normally featuring this variety) when grown in a tunnel (as described above) in December 2014.

A population of approximately 450 seeds was derived from open and self pollinations of 1423 between 2015 and 2016.

The progeny seeds were sown and out of them approximately 250 plants were grown in a tunnel covered by a polyethethylene film for observations and selections for flower size and/or pedicel length and/or pedicel thickness resulted in 8 lines (1496, 1577, 1592, 1593, 1597, 1528, 1521, 1562) which displayed big flowers and/or long pedicels and/or thick pedicels. 1496, 1577, 1592, 1593, 1597, 1528, 1521, 1562, 1593-varieties with big flowers.

Genetic Background 3:

The inventor found a *Scabiosa* plant (of the 1434 background) with slightly bigger (8 cm as compared to 6 cm-normally featuring this variety). Plants when grown in a tunnel (as described above) in December 2014.

A population of approximately 400 seeds was derived from open and self pollinations of 1434 as the female plant between 2015 and 2016.

The progeny seeds were sown and out of them 325 plants were grown in a tunnel covered with a polyethene film for observations and selections for flower size and/or pedicel length and/or pedicel thickness resulted in 4 lines (1555, 1575, 1574, 1550, 1576) which displayed big flowers and/or long pedicels and/or thick pedicels.

1574, 1576, 1555, 1575, 1550-varieties with big flowers and long thick pedicels.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A *Scabiosa atropurpurea* plant selected from the group consisting of SB-15-1483, seeds of which having been deposited under the Budapest Treaty at the Korean Collection for Type Cultures under KCTC13541BP on Jun. 5, 2018; SB-15-1503, seeds of which having been deposited under the Budapest treaty at the NCIMB Ltd. (Ferguson Building Craibstone Estate, Bucksburn. Aberdeen Scotland) under NCIMB43096 on Jul. 11, 2018; SB-15-1504, seeds of which having been deposited under the Budapest Treaty at the Korean Collection for Type Cultures under KCTC13542BP on Jun. 5, 2018; SB-15-1577, seeds of which having been deposited under the Budapest treaty at the NCIMB Ltd. (Ferguson Building Craibstone Estate, Bucksburn. Aberdeen Scotland) under NCIMB43141 on Aug. 6, 2018; SB-16-1593, seeds of which having been deposited under the Budapest treaty at the NCIMB Ltd. (Ferguson Building Craibstone Estate, Bucksburn. Aberdeen Scotland) under NCIMB43139 on Jul. 11, 2018; SB-16-1597, seeds of which having been deposited under the Budapest treaty at the NCIMB Ltd. (Ferguson Building Craibstone Estate, Bucksburn. Aberdeen Scotland) under NCIMB43142 on Aug. 6, 2018; SB-15-1575, seeds of which having been deposited under the Budapest treaty at the NCIMB Ltd. (Ferguson Building Craibstone Estate, Bucksburn. Aberdeen Scotland) under NCIMB43138 on Jul. 11, 2018; SB-15-1574, seeds of which having been deposited under the Budapest treaty at the NCIMB Ltd. (Ferguson Building Craibstone Estate, Bucksburn. Aberdeen Scotland) under NCIMB43140 on Aug. 6, 2018; SB-15-1550, seeds of which having been deposited under the Budapest Treaty at the Korean Collection for Type Cultures under KCTC13543BP on Jun. 5, 2018; SB-15-1592, seeds of which having been deposited under the Budapest Treaty at the Korean Collection for Type Cultures under KCTC13545BP on Jun. 5, 2018; SB-16-1539, seeds of which having been deposited under the Budapest treaty at the NCIMB Ltd. (Ferguson Building Craibstone Estate, Bucksburn. Aberdeen Scotland) under NCIMB43099 on Jul. 11, 2018; SB-16-1576, seeds of which having been deposited under the Budapest Treaty at the Korean Collection for Type Cultures under KCTC13547BP on Jun. 5, 2018; SB-15-1496, seeds of which having been deposited under the Budapest treaty at the NCIMB Ltd. (Ferguson Building Craibstone Estate, Bucksburn. Aberdeen Scotland) under NCIMB43070 on Jun. 5, 2018; SB-16-1528, seeds of which having been deposited under the Budapest treaty at the NCIMB Ltd. (Ferguson Building Craibstone Estate, Bucksburn. Aberdeen Scotland) under NCIMB43071 on Jun. 5, 2018; SB-15-1515, seeds of which having been deposited under the Budapest treaty at the NCIMB Ltd. (Ferguson Building Craibstone Estate, Bucksburn. Aberdeen Scotland) under NCIMB43097, on Jul. 11, 2018; SB-16-1555, seeds of which having been deposited under the Budapest treaty at the NCIMB Ltd. (Ferguson Building Craibstone Estate, Bucksburn. Aberdeen Scotland) under NCIMB43100, on Jul. 11, 2018; SB-16-1562, seeds of which having been deposited under the Budapest treaty at the NCIMB Ltd. (Ferguson Building Craibstone Estate, Bucksburn. Aberdeen Scotland) under NCIMB43101, on Jul. 11, 2018.

2. A method of producing a *Scabiosa atropurpurea* plant, the method comprising:
   (a) crossing *Scabiosa atropurpurea* plants of claim 1;
   (b) recovering seeds following said crossing;
   (c) planting said seeds and growing said seed into plants; and
   (d) selecting a hybrid plant.

3. The method of claim 2, wherein said selecting is according to inflorescence diameter, pedicel length and/or pedicel diameter.

4. A method of developing a cultivated stable plant using plant breeding techniques, the method comprising using the plant or plant part of claim 1 as a source of breeding material for self-breeding and/or cross-breeding.

* * * * *